United States Patent
Galavotti (10) Patent No.: US 9,011,768 B2
(45) Date of Patent: Apr. 21, 2015

(54) DEVICE FOR TREATING BLOOD IN AN EXTRACORPOREAL CIRCULATION

(75) Inventor: Daniele Galavotti, Mirandola (IT)

(73) Assignee: Rand, S.R.L., Medolla (IT)

( * ) Notice: Subject to any disclaimer, the term of this patent is extended or adjusted under 35 U.S.C. 154(b) by 122 days.

(21) Appl. No.: 13/806,002

(22) PCT Filed: Jun. 28, 2011

(86) PCT No.: PCT/IB2011/052833
§ 371 (c)(1),
(2), (4) Date: Dec. 20, 2012

(87) PCT Pub. No.: WO2012/001622
PCT Pub. Date: Jan. 5, 2012

(65) Prior Publication Data
US 2013/0101465 A1 Apr. 25, 2013

(30) Foreign Application Priority Data
Jun. 28, 2010 (IT) .............................. MO2010A0192

(51) Int. Cl.
*A61M 1/16* (2006.01)
*B01D 63/02* (2006.01)
*B01D 63/04* (2006.01)

(52) U.S. Cl.
CPC ........... *A61M 1/1698* (2013.01); *B01D 63/025* (2013.01); *B01D 63/043* (2013.01); *B01D 2313/10* (2013.01); *B01D 2313/38* (2013.01); *B01D 2313/50* (2013.01); *A61M 1/1625* (2014.02); *A61M 1/1629* (2014.02)

(58) Field of Classification Search
CPC .. A61M 1/106; A61M 1/1678; A61M 1/1698
USPC .............................. 604/4.01–6.16; 422/44–48
See application file for complete search history.

(56) References Cited

U.S. PATENT DOCUMENTS

| 4,639,353 A | * | 1/1987 | Takemura et al. | ............... 422/46 |
| 5,706,889 A | * | 1/1998 | Bach et al. | ..................... 165/172 |
| 2005/0163656 A1 | * | 7/2005 | Galavotti | ......................... 422/44 |

FOREIGN PATENT DOCUMENTS

EP     1557185 A1     7/2005

* cited by examiner

*Primary Examiner* — Philip R Wiest
*Assistant Examiner* — Benjamin Klein
(74) *Attorney, Agent, or Firm* — R. Neil Sudol; Henry D. Coleman (57) ABSTRACT

A device for oxygenating blood during extracorporeal circulation includes a box-like body having a first end and a second end opposite thereto and defining therebetween a treatment chamber with an inner surface. The device further includes, in the treatment chamber, at least one exchange unit having at least one flat diaphragm that is impervious to blood and has a major axis and a minor axis. The diaphragm has a winding of hollow microporous fibers. The device further includes an inlet port and an outlet port axially aligned with one another in an alignment direction. A compartment is provided for accumulation and delivery of blood to be treated, another compartment for collecting treated blood, the compartments being located downstream of the inlet port and upstream of the outlet port, between the exchange unit and the inner surface of the treatment chamber. The diaphragm is disposed with the major axis parallel to the alignment direction.

15 Claims, 10 Drawing Sheets

DEVICE FOR TREATING BLOOD IN AN EXTRACORPOREAL CIRCULATION

TECHNICAL FIELD

The invention relates to a device for oxygenating blood during extracorporeal circulation, particularly a blood oxygenator whose three-dimensional structure has a substantially cylindrical shape, that defines a treatment compartment, which has multiple inner elements arranged thereon, wrapped with bundles of layers of capillaries made of a microporous membrane and designed to be externally lapped by blood flowing through the compartment in a direction substantially perpendicular to the capillaries.

The compartment has passages for communication with the outside and is internally equipped with a set of diaphragms and partition elements which are monolithic or monolithically formed, and substantially have a flattened form and outer surfaces with alternating concave and convex areas, which are configured to impart a wavy motion to blood flow, thereby increasing areas and cycles of contact between blood and the bundles of hollow fibers and hence improving gas exchange.

The structure of the device for treating blood during extracorporeal circulation is designed to be coupled to an additional blood treatment device, such as a heat exchanger located upstream from the inlet for the blood to be treated that comes from the patient.

BACKGROUND ART

Disposable oxygen exchanging devices, known as oxygenators, have been long known and used in the medical field, with the purpose of releasing oxygen to blood and removing excess carbon dioxide from patient blood during extracorporal circulation treatments.

These prior art devices consist of substantially cylindrical bodies, which enclose an oxygenation chamber with a gas exchanging unit arranged therein.

The latter typically consists of a multitude of hollow fibers, which are arranged substantially parallel to each other and to the longitudinal axis of the cylindrical body, have a lumen as large as a few hundreds of microns, and are formed of a flexible membrane, which is only gas-and not fluid-permeable.

The ends of the hollow fibers are incorporated in two corresponding solid connection elements, known as "pottings", which are typically formed of polyurethane-based glues.

In practice, the container bodies of these oxygenator devices, hereinafter simply referred to as oxygenators, have a first blood inlet and outlet pair, with blood being forced to flow in a predetermined path within the oxygenation chamber, and to lap the hollow fibers in a flow direction substantially perpendicular thereto, thereby becoming richer in oxygen and releasing excess carbon dioxide.

The cylindrical body also has a second inlet and outlet pair, designed both for supplying oxygen gas, in pure form or diluted with other gases, such as nitrogen, and for discharging the carbon dioxide released to blood during oxygenation.

These oxygenator devices are typically combined with heat exchangers, which are required for temperature control of the blood flowing in the extracorporeal circuit of the patient to be treated, and which typically use water "treated" by a heating device or cooling water to add or remove heat from patient's blood, and are generally known as "heaters" or "coolers" or otherwise generally defined as "temperature baths".

Typically, for operation of these oxygenators, after such passage through a temperature control apparatus to reach a desired temperature, the blood to be oxygenated that comes from the patient and is carried by a transport conduit shall enter the oxygenation chamber through the inlet therefore, lap the multitude of hollow fibers having oxygen, or a mixture of oxygen and other diluting gases, flowing therein, receive oxygen and simultaneously release carbon dioxide as a result of differential concentrations, and eventually flow out of the outlet in an oxygen-enriched state, to finally reach the patient through a return connection line.

Oxygen, or the oxygen-containing gas mixture, enters its inlet and is released to blood while carbon dioxide is released by blood to the depleted oxygen that flows in the hollow fibers and us discharged through the outlet.

The motion of blood flow that comes from the patient, passes through the oxygenator and goes back to the patient is typically generated and maintained using a pump that may be mounted along an extracorporeal circuit that establishes connection between the patient and the oxygenator.

The pump action generates a pressure higher than atmospheric pressure in the oxygenator, which is sufficient to overcome the sum of the mechanical resistances encountered by blood as it flows through the treatment chamber that contains the hollow fibers, through the conduits that connect the various devices and those of the peripheral circulatory system of the patient, to ensure that circulation is maintained active all along the path defined by the extracorporeal circuit.

An additional requirement to be met by these oxygenators is to provide an exchange surface area that is optimized relative to their overall size, which has to be maintained within strict limits both due to bulk limitation and handling requirements, and because a volume of blood has to be removed from the patient to fill the device and the circuit attached thereto, even though it is diluted with suitable salines.

An oxygenator as described above is known from U.S. Pat. No. 5,817,278.

This patent discloses an oxygenator having a cylindrical body which is composed of an outer wall and an inner wall, arranged in concentric relation to the outer wall and having a smaller diameter, so that a gap, forming the oxygenation chamber, is defined between these inner and outer walls.

This chamber, which has inlet and outlet paths in communication with the outside, holds a set of hollow fibers arranged therein, which are made, as mentioned above, from a membrane that is only permeable to gases, and in which oxygen is caused to flow.

This set of hollow fibers comprises fibers in such number as to circumscribe the inner wall and wrap it until it laps the outer wall, and is kept at a distance therefrom at certain predetermined points by means of a series of longitudinal ribs that project out of the facing surfaces of the inner and outer walls and act as spacers.

Thus, a plurality of free longitudinal passages remain between the set of hollow fibers and the inner and outer walls, which passages are filled with the blood flow as it passes through the oxygenator and generate a substantially wavy flow that passes through the winding of hollow fibers thereby capturing the oxygen flowing therein and releasing the carbon dioxide carried to the outside.

Another oxygenator device is known from patent EP 1 557 185.

This patent discloses an oxygenator having, like the one described above, a hollow cylindrical body that defines an internal oxygenation (or exchange) chamber within which a winding of hollow fibers is arranged.

Once again, the ends of the hollow fibers are embedded in two corresponding end elements known as "pottings", and formed of plastic material.

The oxygenation chamber is composed of two half-chambers, each holding a corresponding winding of hollow fibers, so that the latter are perpendicular to an inlet and an outlet for the blood to be oxygenated, and in opposed relation.

Each of the windings of hollow fibers defines a smaller chamber at its center, containing a diaphragm, that consists of a solid and substantially flat body, hence impermeable to blood flow, whose ends are held in contact with the winding of hollow fibers.

This diaphragm has a cross section with surfaces that push back the blood flow as it impinges against it in the path between the inlet and the outlet and deflect it towards the winding of hollow fibers, thereby imparting a wavy motion in the blood flow to be oxygenated, which is caused to pass through the winding of hollow fibers at multiple areas, thereby creating the desired exchange between oxygen and blood and between the carbon dioxide released from the blood and the hollow fibers that form the winding.

Two adjacent, isolated chambers are defined in the body of the oxygenator according to this document, which chambers are arranged in mirror-like arrangement with respect to a median plane of symmetry.

The first chamber uses a winding of non porous plastic capillaries for thermostating the blood that laps the exterior surfaces thereof, with the thermostating fluid, typically water, flowing in the capillaries; on the other hand, the second chamber uses a winding of hollow fibers arranged therein which are formed of a microporous membrane, and are used to transfer oxygen to the blood that laps the exterior surfaces of these hollow fibers, while oxygen flows therein.

Furthermore, a series of longitudinal parallel passages are provided, also in mirror-like arrangement, which facilitate the passage of blood flows and have the purpose of breaking the laminar flow and improve the effectiveness of the oxygenation and carbon dioxide removal process.

This prior art suffers from certain drawbacks.

A first drawback is that the increase of pressure losses caused in prior art oxygenators by resistance to blood flow motion damages the red cells membranes and causes hemolysis, i.e. red cell (or erythrocyte) destruction.

A second drawback is that prior art oxygenators require their oxygenation (and exchange) chambers to be filled with considerable volumes of blood, to be withdrawn and removed from the patient to fill the conduits of an extracorporeal circuit, which volumes are possibly compensated for with additional adequate volumes of blood compatible diluents.

A third drawback is that prior art oxygenators tend to be exposed to quick deterioration of gas exchange performance.

A fourth drawback is that if prior art oxygenators are not used within a short time from their fabrication and are not stored using criteria that can ensure stable effectiveness thereof, they tend with time to be exposed to degradation of the components mainly made of plastic materials.

This degradation may generate deformations of components and thus create undesired gaps or apertures that will act as free passages for blood that will flow through them without previously lapping the hollow fibers and without being adequately oxygenated and washed out of excess carbon dioxide, before reaching back the patient.

SUMMARY OF THE INVENTION

It is an object of the invention to improve the prior art.

Another object of the invention is to provide a device for treating blood during extracorporeal circulation that allows satisfactory oxygenation of patient's blood, relative to its size, that should be as small as possible.

A further object of the invention is to provide a device that only requires withdrawal of small amounts of blood from the patient, to be filled and operate properly.

Another object of the invention is to provide a device that can operate even at very low pressures and for long periods of time, while preserving the integrity of red cell membranes.

Yet another object of the invention is to provide a device that can adequately and consistently oxygenate the blood flow that passes through it during use and for the whole life of the device, in spite of progressive and inevitable aging and degradation of materials.

In one aspect, the invention provides a device for oxygenating blood during extracorporeal circulation as defined in claim 1.

Therefore, the invention provides the following advantages:

improving exchange capacity (also known as mass transfer) as compared with prior art oxygenators;

reducing the assembly steps;

having blood inlet and outlet connections of such shape as to allow interconnection of the other elements of the extracorporeal circuit in a quick and safely hermetic manner, thereby avoiding any undesired blood stagnation;

forming a three-dimensional structure that comprises monolithic diaphragms wrapped with successive layers of microporous plastic capillary fibers, which are woven together and not bonded, are disposed in either random or regular arrangement and are perfectly biocompatible;

providing a distribution of contact areas having alternate concave and convex surfaces, which generally improve gas exchange with blood;

placing therein a plurality of monolithic elements in series arrangement, which are adapted to be lapped by blood, and to create minimized resistance thereagainst, while optimizing treated blood volume and gas exchange between the oxygen mixture conveyed into the capillary fibers and the blood flowing through the device; and providing an oxygenator device that can be easily coupled both with a heat exchanger, that does not require the use of a temperature-controlling liquid and with a heat exchanger that uses a temperature-controlling liquid.

BRIEF DESCRIPTION OF THE DRAWINGS

Further features and advantages of the invention will be more readily apparent upon reading of the description of a preferred, non exclusive, embodiment of a device for oxygenating blood during extracorporeal circulation according to the invention, which is shown as a non limiting example by the annexed drawings, in which.

DESCRIPTION OF EMBODIMENTS OF THE INVENTION

Figures 1, 3:
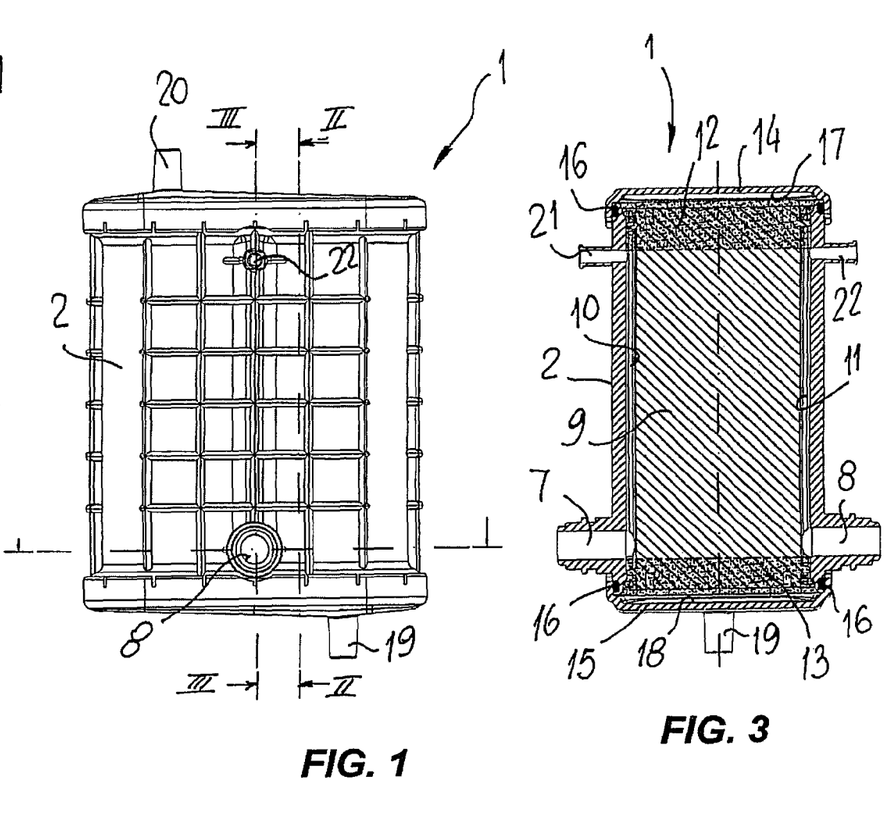
FIG. 1 is a front view of a device for oxygenating blood during extracorporeal circulation according to the invention.
FIG. 3 is a longitudinal sectional view of the device for oxygenating blood during extracorporeal circulation, as taken along a plane III-III of FIG. 1.
Figure 2:
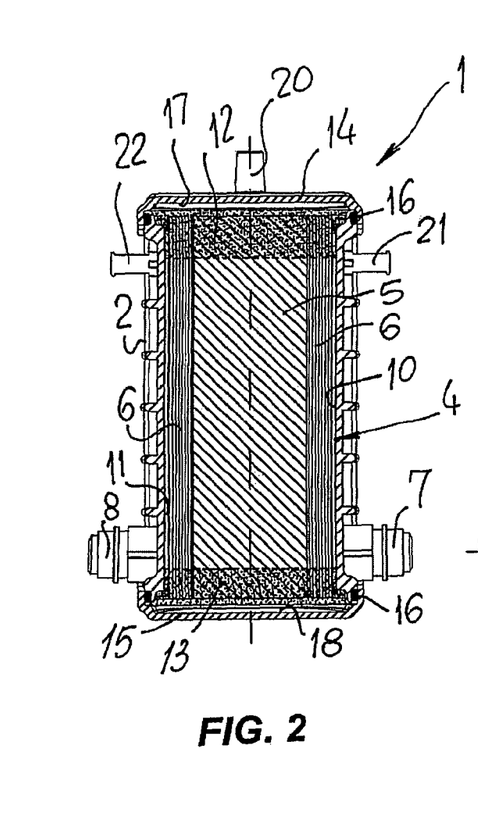
FIG. 2 is a longitudinal sectional view of the device for oxygenating blood during extracorporeal circulation, as taken along a plane II-II of FIG. 1.

Referring to FIGS. 1, 2, 3, it can be appreciated that in a first embodiment, a device for treating blood during extracorporeal circulation, is generally designated by numeral 1 and comprises a box-like body 2 having a substantially cylindrical shape, that defines a blood treatment chamber 3, with an exchange unit 4 arranged therein, comprising a plurality of diaphragms wrapped with bundle windings of a plurality of hollow fibers designated by numeral 6.

It shall be noted that, in the following exemplary embodiment, the term "treatment" is intended as oxygenation of blood flowing through the device 1.

Figure 4:
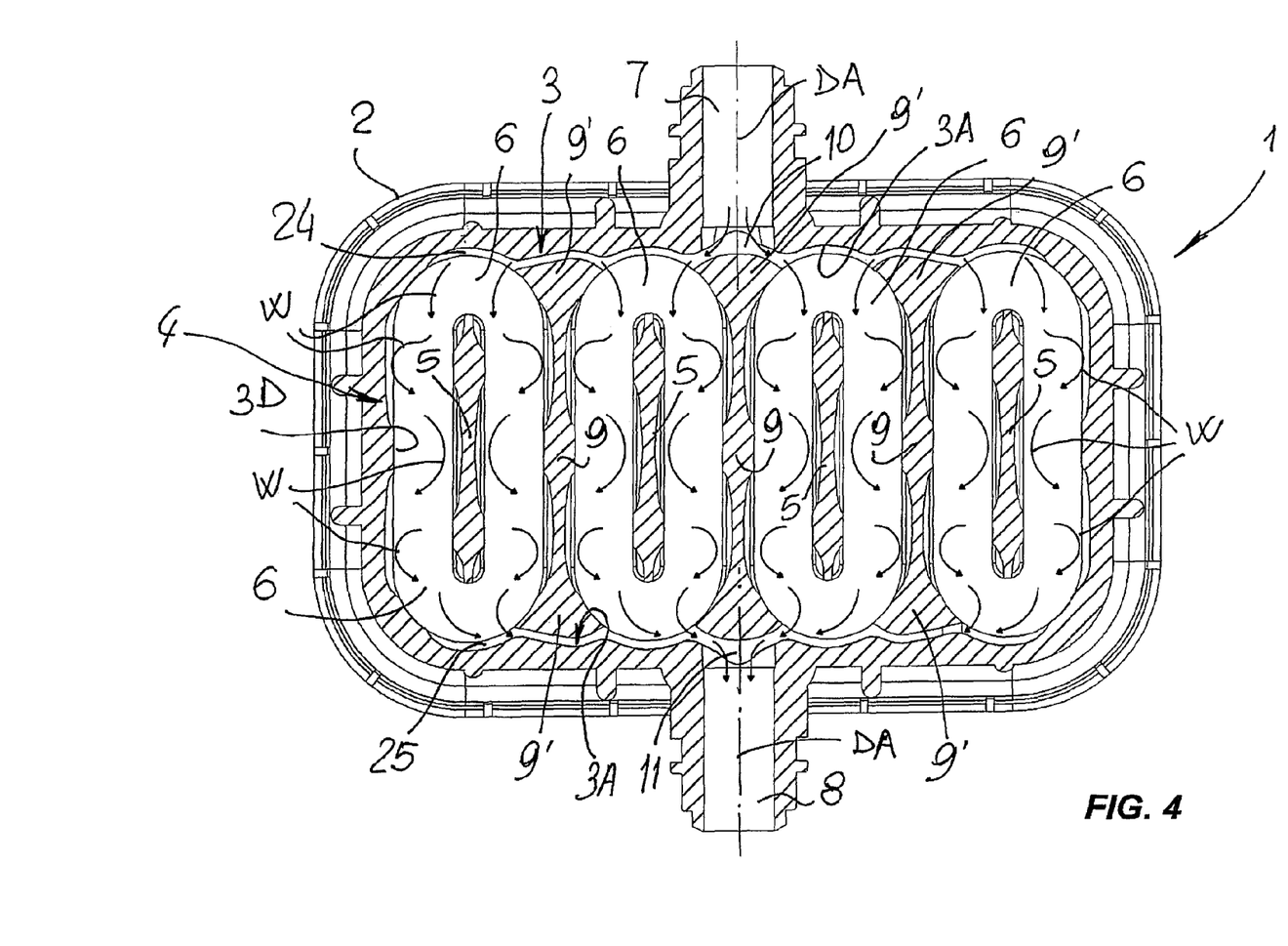
FIG. 4 is a cross sectional view of the device for oxygenating blood during extracorporeal circulation, as taken along a plane IV-IV of FIG. 1.

The box-like body 2 has an inlet port 7 for the blood to be treated and an outlet port 8 opposite to and aligned with the inlet port 7 which defines therewith an alignment direction designated in FIG. 4 by the line "DA".

As shown in FIG. 4, all the diaphragms 5, that will be described in detail below, are arranged parallel to the alignment direction "DA" and the windings 6 of hollow fibers are also arranged with their greater axes parallel to this direction.

The windings 6 have partition elements 9 therebetween, also described in detail below, which have the purpose of maintaining them separate and, like the diaphragms 5, have their longitudinal greater axes arranged parallel to the alignment direction "DA".

As shown in FIGS. 2, 3, 4, two compartments, referenced 10 and 11 respectively, are defined between the exchange unit 4 and the inner surface of the treatment chamber 3, which is referenced 3A, where the blood to be treated that comes from the inlet port 7 accumulates in the compartment 10 and the treated blood before discharge through the outlet port 8 is collected in the compartment 11.

As shown in FIGS. 2 and 3, the compartments 10 and 11 extend along the windings 6 and the hollow fibers that compose the latter have their ends embedded in two corresponding fixation elements, known as "pottings" and referenced 12 and 13 respectively.

The body 2 has closing covers 14 and 15 that hermetically seal its ends, with interposed annular seals 16.

Still referring to FIGS. 2 and 3, it may be seen that two additional chambers, referred to as collecting chambers and referenced 17 and 18 are defined between the covers 14 and 15 and the two pottings 12 and 13.

The chamber 17 is used for accumulation of the oxygen gas that is designed to flow in the hollow fibers of the windings 6, whereas the chamber 18 is used for accumulation of the carbon dioxide that, after the exchange in the treatment chamber 3, is released from blood to the depleted oxygen flowing in the hollow fibers, typically due to differential concentration.

Such carbon dioxide comes out of the collection chamber 18 of the device 1 through a special outlet 19 formed in the cover 15, whereas oxygen enters the collection chamber 17 through an inlet 20 formed in the cover 14.

The body 2 also has two additional inlet ports, referenced 21 and 22, which provide communication between the outside environment and the compartment 10 and the compartment 11 respectively, to discharge any air volume contained therein.

Figure 4A:
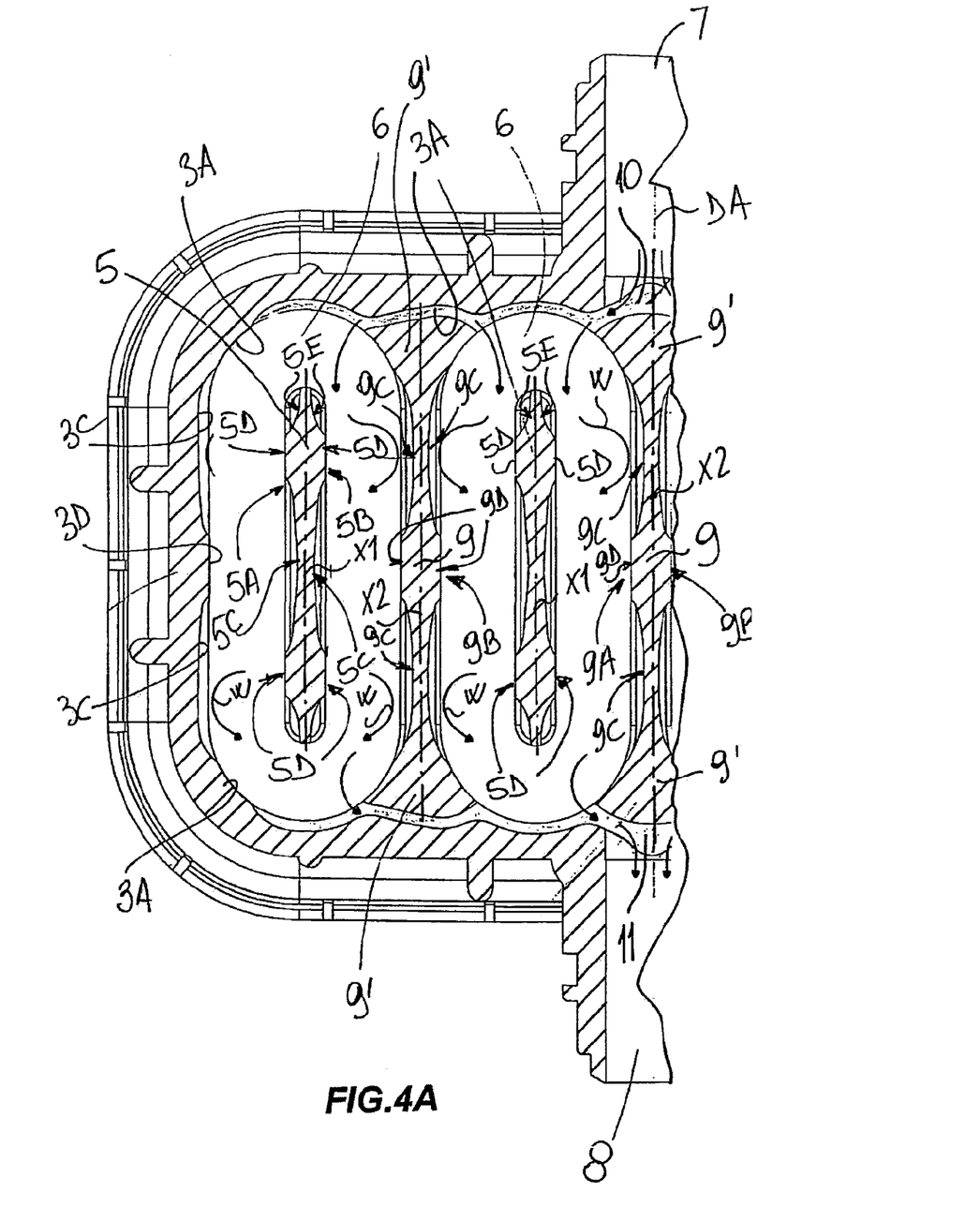
FIG. 4A is a greatly enlarged view of a left portion of the blood oxygenating device as shown in FIG. 4, as viewed by an observer.

Referring to FIG. 4A, the greater axes of the diaphragms 5, referenced "X1" and the partition elements 9, referenced "X2" are all parallel to the alignment direction "DA" and hence are also parallel to each other.

Figure 12:
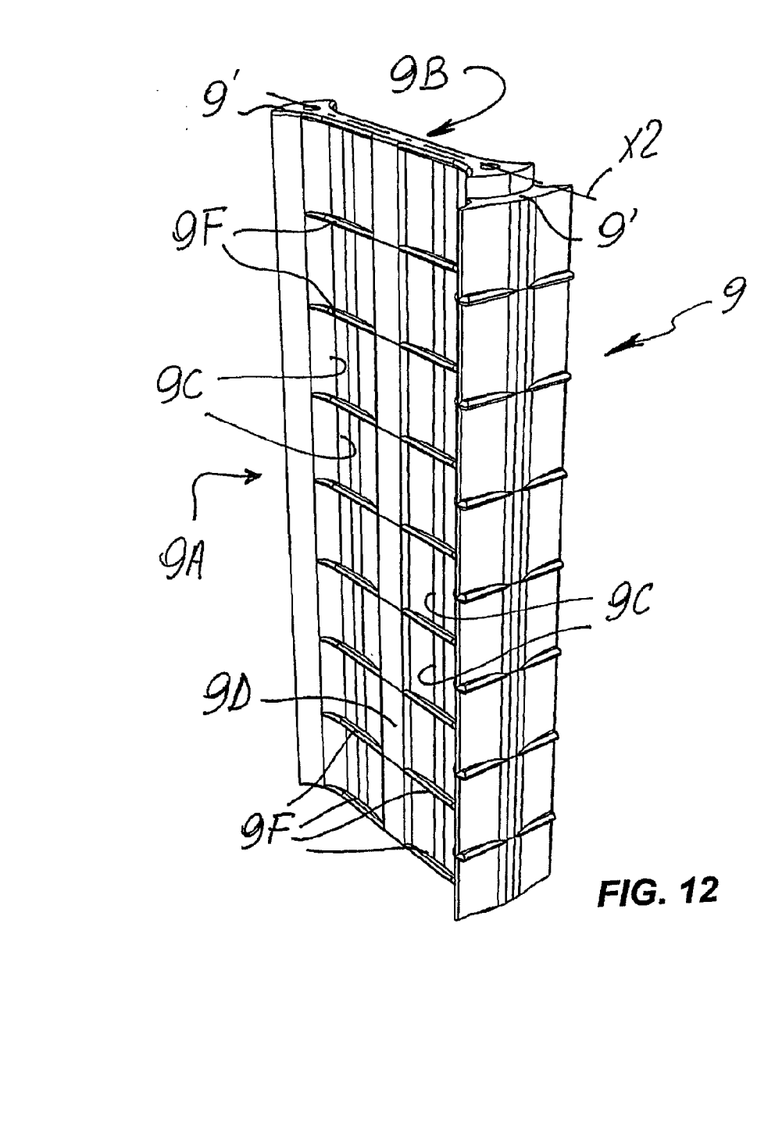
FIG. 12 is an enlarged perspective view of a partition element that is used in the blood oxygenating device.
Figure 13:
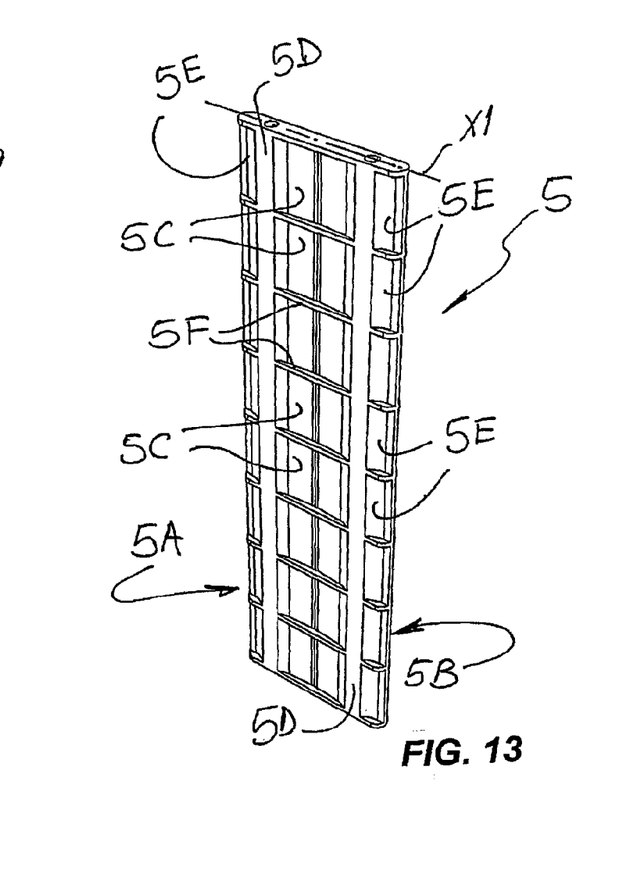
FIG. 13 is an enlarged perspective view of a diaphragm wrapped with bundles of hollow fibers that can be placed in the blood oxygenating device of the invention.

More in detail, also referring to FIGS. 12 and 13, it shall be noted that each of the diaphragms 5 and each of the partition elements 9 have two larger faces in parallel opposed arrangements, referenced 5A and 5B and 9A and 9B respectively, with blood flow conveying concavities, referenced 5C and 9C respectively formed thereon alternated to convex or planar sections 5D and 9D, the latter forming straight longitudinal ribs designed to maintain the windings of hollow fibers 6 separate from the surfaces of the larger faces 5A, 5B and 9A, 9B.

Pairs of semi-concavities 5E, that continuously extend the apertures 5C formed in the middle area of the diaphragms 5 are also found at the end edges of the diaphragms 5.

Likewise, further conveying concavities 3C are formed in the inner surface 3A of the treatment chamber 3, alternated to convex or planar sections 3D.

Transverse ribs 5F and 9F are also formed on the concavities 5C, 5E of the diaphragms 5 and the concavities 9C of the spacer elements 9, for supporting the windings 6 and for cooperating with the straight ribs 5B and 9B to maintain the blood flow compartments 5C, 5E and 9C perfectly open.

More in detail, the cavities 3C and 9C appear to be in mutual alignment positions, whereas the concavities 3A are aligned with the convex or planar sections 3D, 5D, 9D: this arrangement has the purpose of imparting a wavy motion to the blood flows that lap the hollow fibers of the windings 6, as shown by the arrows "W", for improved gas exchange.

Also referring to FIG. 4, each winding 6 appears to be interposed between two partition elements 9 or between a partition element 9 and the inner surface 3A and 3D.

In the embodiment of the device as shown in FIG. 4, the partition elements 9 are shown to have enlarged ends 9' whose shape allows them to be tangent to the outer surfaces of the windings 6, although they define two free passages 24 and 25 between two contiguous partitions, for the entry and exit of blood flows into and from the windings 6.

Figure 5:
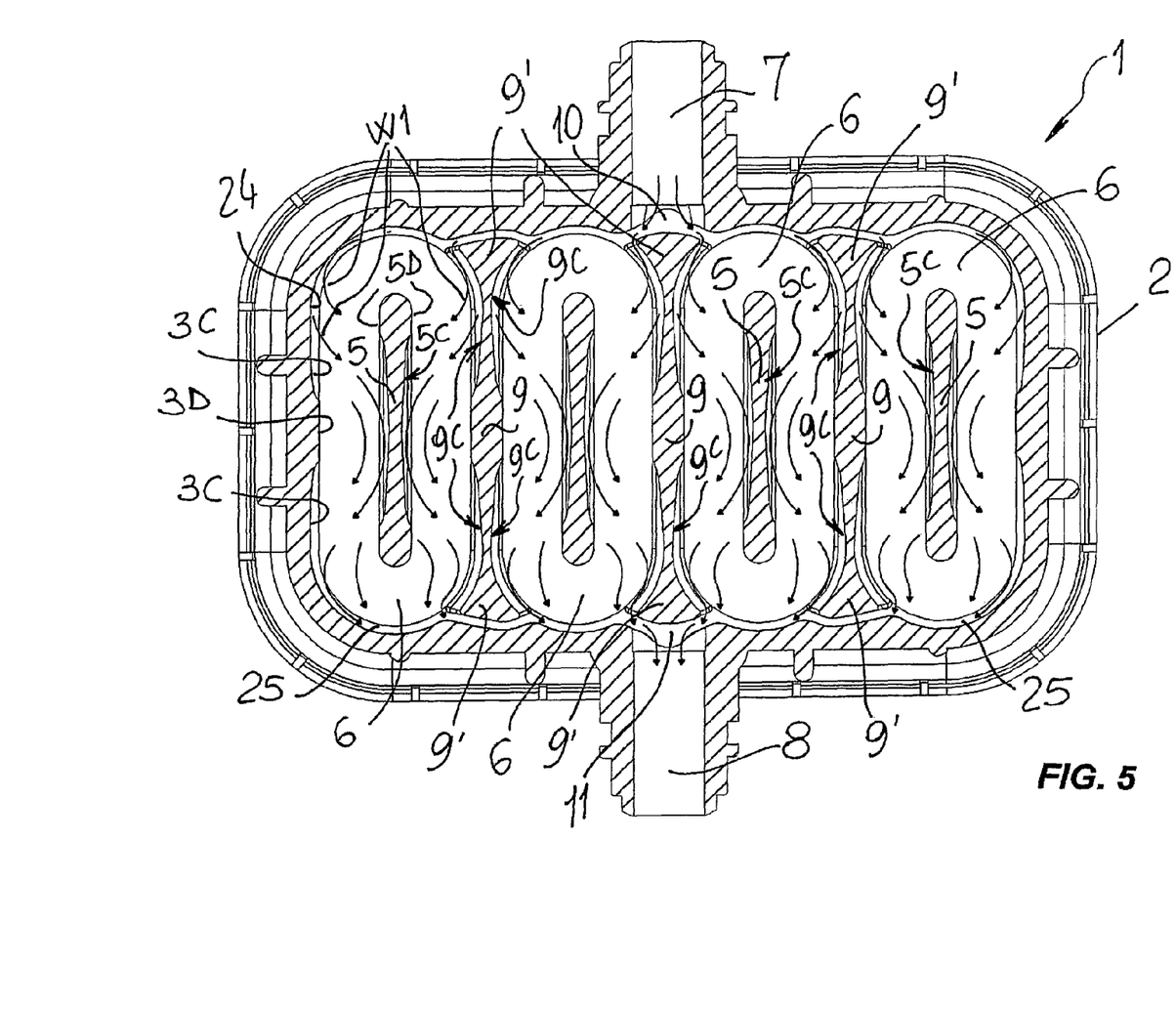
FIG. 5 is a cross sectional view of a second alternative version of the section as shown in FIG. 4.

FIG. 5 shows a possible distribution of the free passages 24 and 25, which are located in the device 1 tangent to the outer surfaces of the windings 6, as shown by arrows "W1", with all the other construction elements identical to those as shown in FIG. 4.

Figure 6:
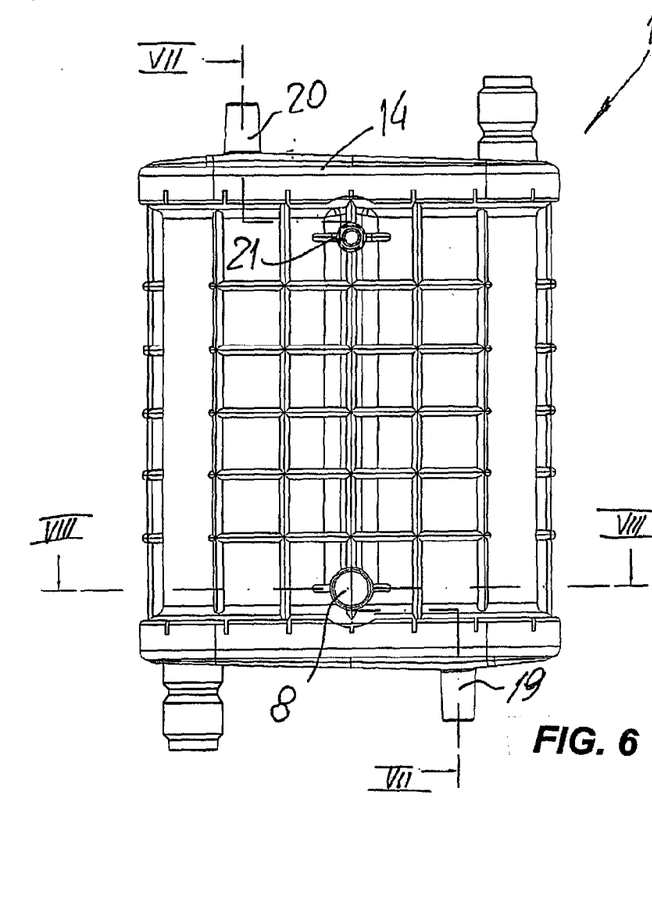
FIG. 6 is a front view of a device for oxygenating blood during extracorporeal circulation according to the invention, according to a second possible embodiment, in which a heat exchanger device is integrated.
Figure 7:
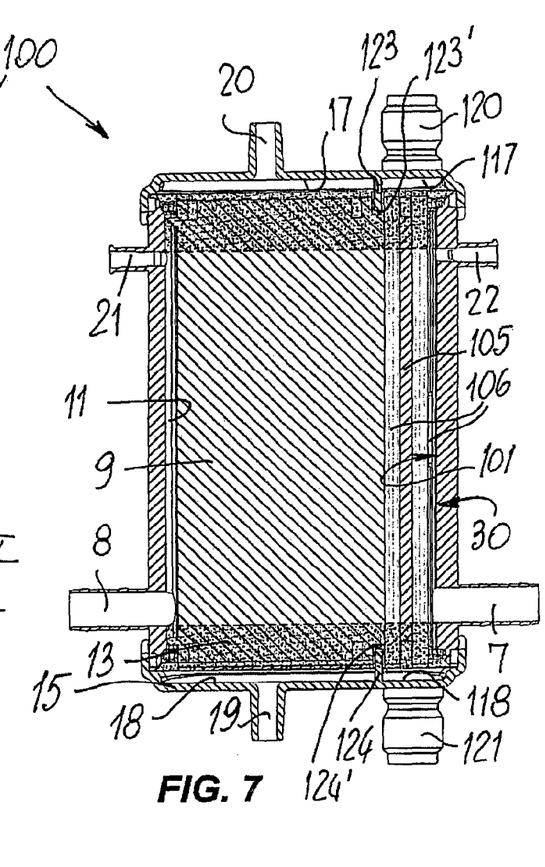
FIG. 7 is a longitudinal sectional view of the version of the blood oxygenating device of FIG. 6, as taken along a plane VII-VII.
Figure 8:
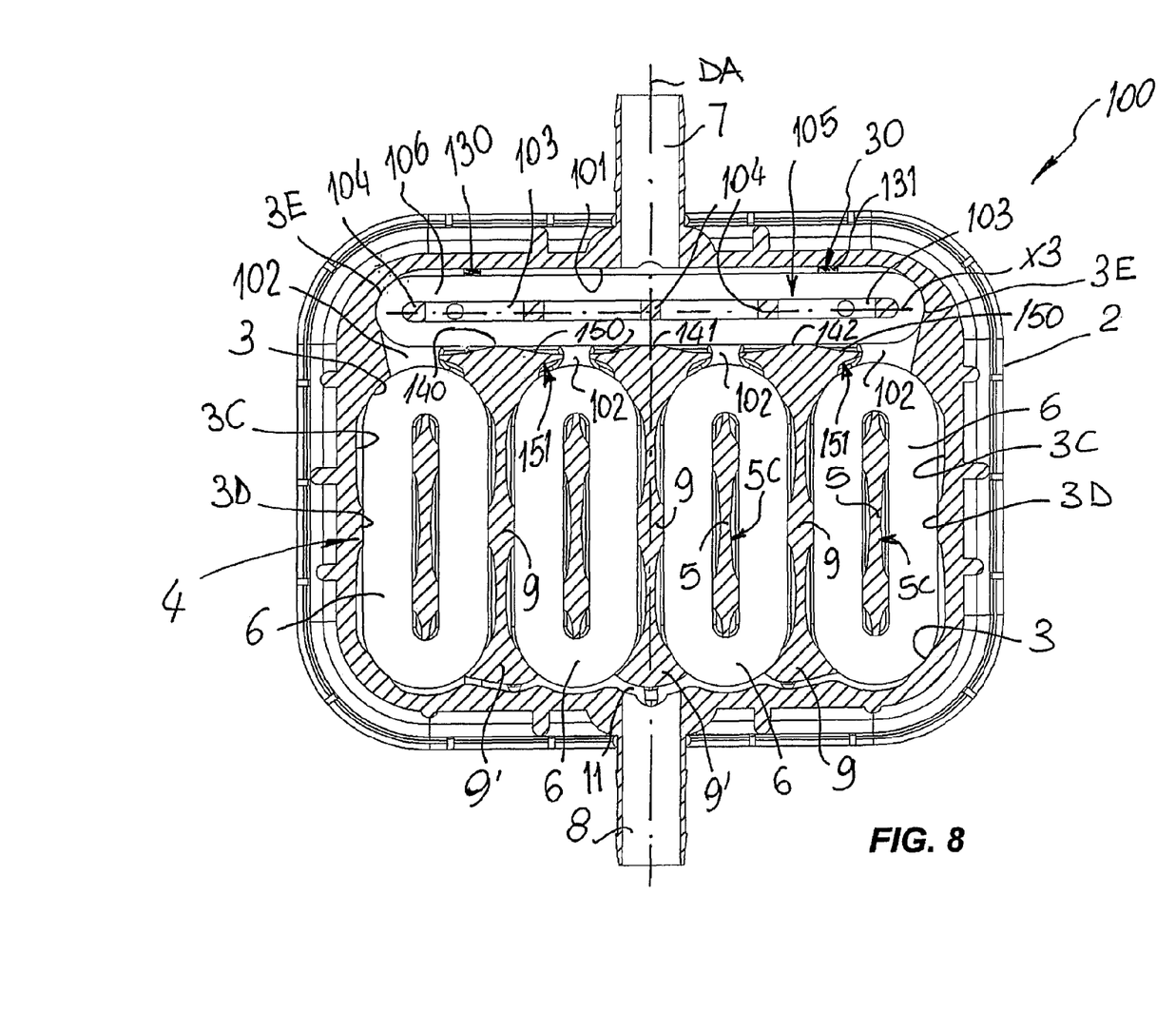
FIG. 8 is a cross sectional view of the blood oxygenating device of FIG. 6, as taken along a plane VIII-VIII.

Referring to FIGS. 6, 7, 8, there is shown an advanced embodiment of the device 1 for treating blood during extracorporeal circulation, in which a temperature-control unit 30 for controlling the temperature of the blood to be treated, is integrated in the body 2, in addition to the exchange unit 4.

In FIGS. 6, 7, 8 same reference numerals are used to designate same elements, common to the other embodiments of the device 1 for treating blood during extracorporeal circulation, and to facilitate location of these common elements, whereas the device for treating blood during extracorporeal circulation according to this advanced embodiment has been generally referenced 100.

As shown in greater detail in FIG. 8, a temperature control chamber 101 is formed downstream from the inlet port 7, and is connected with the treatment chamber 3 via passages 102.

The temperature control chamber 101 has a winding of hollow fibers 30 therein, which has wholly impermeable walls, is referenced 106 and is wound on a central grid-like core, i.e. having apertures or passages 103 defined between a plurality of lattice elements 104.

The central grid 105 has a greater axis "X3" which is oriented substantially perpendicular to the alignment direction "DA".

The winding 106 of hollow fibers is mounted in the treatment chamber 3 in contact with the inner walls thereof, which delimit size according the axis X3 in the two end areas, referenced 3E.

The winding 106 is also delimited in a direction perpendicular to the axis "X3" and to a limited height of the device 100, both by two ribs 130 and 131 raising from the temperature control chamber 101 and by protrusions 140, 141, 142 formed in the enlarged ends 9' of the spacer elements 9.

Further spacing ribs 150 and further spacing ribs 151 extend transverse to the protrusions 140, 141, 142, to maintain a gap between the winding 106 and the passages 102 and to maintain a gap between the winding 6 and the passages 102.

A fluid (such as water) previously heated or cooled, as needed, is designed to flow in the hollow fibers of the winding 30, and to enter the impermeable capillaries through an inlet port 121 formed in the cover 15 and an accumulation chamber 118 and, once it has flown past the winding 106, it collects in a collection chamber 117 and is discharged through an outlet port 120 formed in the cover 14.

Two barriers, referenced 123 and 124 respectively, extend from the inner surfaces of the covers 14 and 15 into their respective pottings 12 and 13, and are hermetically sealed therein by seals 123' and 124'.

The barriers 123 and 124 hermetically separate the chamber 17 from the accumulation chamber 117 and the chamber 18 from the collection chamber 118.

The treatment chamber 3 is placed, as described above, downstream from the temperature control unit 30, and houses the treatment unit 4, also described above.

The skilled person may easily understand that the predetermined number of windings 6 of hollow fibers may be different from what is shown, the number of windings being determined, for instance, by the patient's size and hence by the blood flow to be treated.

Likewise, the number of diaphragms 5 and partition elements 9 may also change according to the number of windings that have to be arranged in the treatment chamber 3.

Figure 9:
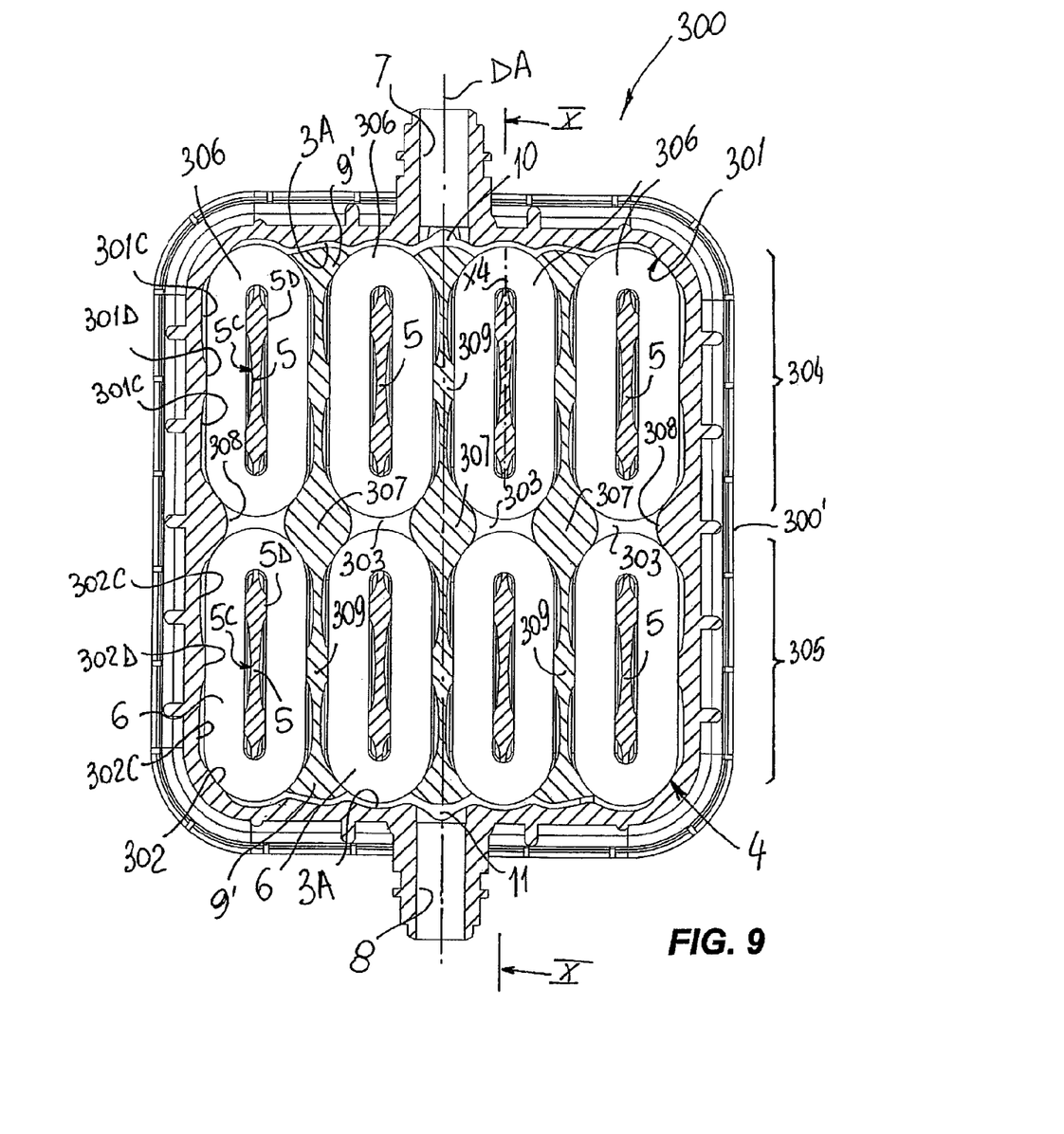
FIG. 9 is a cross sectional view of the blood oxygenating device according to a third possible embodiment, which is also equipped with a heat exchanger device.
Figure 10:
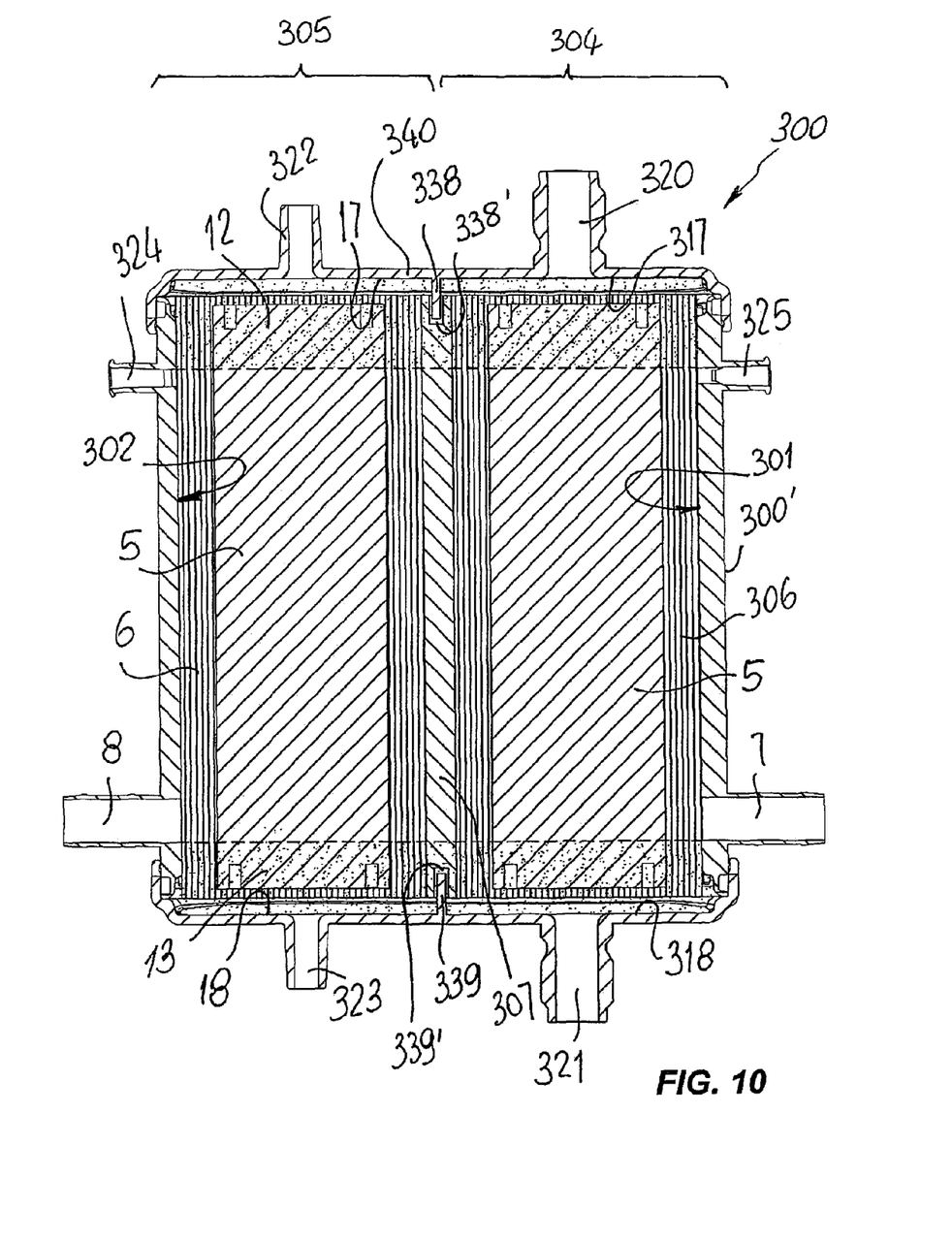
FIG. 10 is a longitudinal sectional view of the blood oxygenating device of FIG. 9, as taken along a plane X-X.
Figure 11:
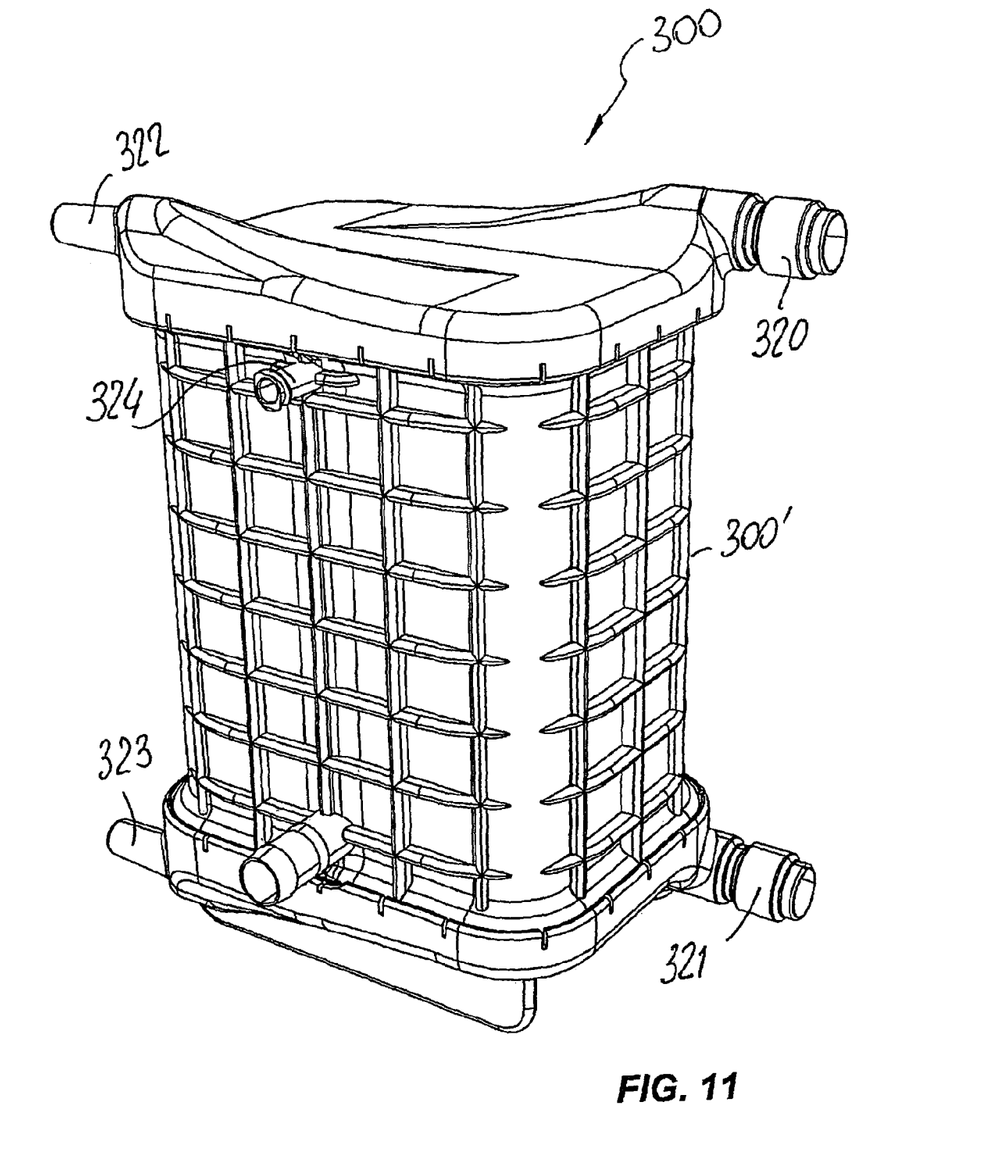
FIG. 11 is a general perspective view of the device for oxygenating blood according to the model as shown in FIGS. 6, 7 and 8.

Referring to FIGS. 9, 10, 11, there is shown a further embodiment of a device for treating blood during extracorporeal circulation according to the invention, in which a temperature control unit for controlling the treated blood is also integrated.

Also in these figures, the elements common to the above described embodiments are designated by the same reference numerals, whereas the device is generally referenced 300.

The device 300 comprises a box-like body 300' in which two contiguous treatment chambers 301 and 302, hydraulically connected by connection passages 303 are defined.

In practice, the two treatment chambers 301 and 302 define a first section for temperature control of blood, generally referenced 304 and a second blood section for oxygenation of temperature-controlled blood, generally designated 305.

The first chamber 301 has arranged therein windings 306 of wholly impermeable capillaries, in which a temperature control fluid flows, typically water, previously heated or cooled as therapeutically needed by a patient, whereas the second chamber 302 has arranged therein second windings 6 of gas-permeable, liquid-impermeable hollow fibers, in which oxygen or a mixture of oxygen and other blood compatible gases flow.

Like in the case of FIG. 4, a compartment 10 is defined in the first chamber 301, for accumulation of blood to be treated, coming from a patient, and a second compartment 11 is defined in the second chamber 302, for accumulation of blood after treatment and before return to the patient through the outlet port 8.

As shown in FIGS. 9 and 10, the conformation and distribution of the first windings 306 and the second windings 6 in the device 300 are substantially identical and symmetrical with respect to the alignment direction "DA" that coincides with a median axis of the device 300.

Once again both the first windings 306 and the second windings 6 are wound on parallel diaphragms, which are referenced 5 for both windings, as they are substantially identical.

Like in the above described embodiments, the partitions 5 have cavities 5C and convex or planar sections 5D to impart a wavy motion to blood as it flows through the device 300.

Likewise, the first windings 306 and the second windings 6 are both separated by partition elements 309 which only differ from the corresponding partition elements 9 of the previous embodiments in that, at the passages 303, they are joined together by connection parts 307 having such a shape as to form concurrent ends of each pair of partition elements 309 aligned in the alignment direction "DA".

The inner walls 3A of the temperature control chamber 301 and the oxygenation chamber 302 also have alternating cavities 301C and 302C and planar sections 301D and 302 and, at the passages 303 they have raised ribs 308, substantially corresponding to a half-portion of a connection part 307.

Referring to FIG. 10, it can be noted that the body 300' has an upper cover 340 and a lower cover 341 and that both the impermeable capillaries of the first winding 306 and the microporous hollow fibers of the second winding 6 have their respective ends fixed in pottings, referenced 12 and 13.

The body 300' is closed by corresponding end covers 340 and 341, wherein are respectively obtained, in the cover 340 an inlet 322 for oxygen or a mixture of oxygen and other biocompatible gases, and an outlet port 320 for the temperature control fluid, while an outlet 323 for the carbon dioxide released from blood and an inlet port 321 for the temperature control fluid are formed in the cover 341.

Chambers 317 and 318 for collecting and accumulating temperature control fluid respectively and chambers 17 and 18 for collecting oxygen and carbon dioxide respectively are defined between the covers 340 and 341 and the corresponding pottings 12, 13.

The chambers 17, 317 and 18, 318 are hermetically sealed by barriers 338 and 339 which extend into their respective pottings 12 and 13 with corresponding seals 338' and 339' interposed therebetween.

This third embodiment of the device 300 also has vents for the escape of any air contained both in the temperature control section, referenced 325 and in the oxygenation section, referenced 324.

The operation of the device for treating blood during extracorporeal circulation according to the invention will be now described, first with reference to the embodiment as shown in FIGS. 1 to 5, and then with reference to the embodiments as shown in FIGS. 6 to 8 and 9 to 11.

Referring to the first embodiment, the blood to be treated, i.e. oxygenated, that comes from a patient, typically through an extracorporeal conduit, enters the device 1 through the inlet port 7 located in the lower portion of the box-like body 2, to fill the compartment 10 from bottom to top, thereby removing any air bubbles from this filling step, by pushing them towards the access port 22 from which they are ejected.

Therefore, blood progressively fills the whole compartment 10 and then flows into the treatment chamber 3 through the free passages 24 or (see FIG. 4) the free passages 25.

In order to be circulated, blood is exposed to a pressure above atmospheric pressure, generated by a pump that is mounted in the extracorporeal circuit, which pressure causes it to flow through the hollow fibers that form the windings 6, and lap their surface.

As shown in FIG. 4, blood contacts the windings 6 at the smaller-area portions thereof, and flows between the hollow fibers thereby encountering an overall smaller resistance to its flow.

Likewise, also as shown in FIG. 5, blood flows between the hollow fibers in substantially oblique directions.

As they flow through the hollow fibers, blood flows are deflected by the cavities 3C, 5C, 5E, 9E, formed in the inner surface 3A of the treatment chamber 3, in the larger faces 5A and 5B and in the opposite ends of the diaphragms 5 and in the larger faces 9A and 9B of the partition elements 9 respectively, thereby assuming a wavy motion pattern, as shown by arrows "W" and "W1", which affords wider and longer contact between blood and the outer porous surfaces of the hollow fibers that form the windings 6.

Oxygen, or a mixture of oxygen and other gases flows in the hollow fibers, and has such a concentration as to be able to pass through the porous walls of the fibers to bind with hemoglobin in blood, which on the other hand releases carbon dioxide that enters the hollow fibers through the porous membrane and mixes with depleted oxygen.

Such oxygen or mixture of oxygen and other gases is introduced through the inlet 20 formed in the upper cover 14 of the device 1, accumulated in the collection chamber 17 and introduced therefrom into the hollow fibers, whereas carbon dioxide collects with depleted oxygen in the collection chamber 19 and then evacuated through the outlet 19 formed in the lower cover 15.

As further shown in FIGS. 4 and 5, the treatment unit 4, i.e. the assembly of windings 6, allows the actual exchange surface to be increased or decreased as needed, by arrangement of a predetermined number of windings 6 in the treatment chamber 3 at constant or variable center-to-center distances.

It shall be further noted that the provision of a number of multiple and modular windings 6, as compared with a single winding having an exchange surface equal to the sum of all the multiple and modular windings, affords easier flow of blood, which encounter a reduced resistance to its motion, such resistance being divided among the various multiple and modular windings whose size is smaller than a whole single winding.

Once blood has flown past a temperature control device, which regulates its temperature to the temperature of the patient's body or to the therapy that the patient has to undergo, and has also flown past all the windings 6 and is thus oxygenated, it collects in the compartment 11 and flows out of it through the outlet port 11, to reach the patient.

Any air bubble still present in blood and in the compartment 11, will be ejected through the access port 21 which, like the access port 22, is formed in the higher portion of the box-like body 2.

Referring to the second embodiment of the device 110, it can be noted that blood follows a path similar to that of the previous embodiment, except that, once blood has entered the device 100, it laps the winding of hollow fibers 106 in which a fluid (typically water) previously heated or cooled as needed, flows.

Thus, once the blood to be treated has flown past the inlet port 7, it fills the temperature control chamber 101 in which it is heated (or cooled) by convection, by lapping the hollow fibers that form the winding 106.

Then, blood flows through the passages 102 and fills the treatment chamber 3 in which it receives oxygenation as described above, before reaching back the patient, in an oxygenated and temperature-controlled state.

Referring to the third embodiment of the device 300, the blood to be treated, that comes from a patient undergoing therapy enters the device 300 through the inlet port 7, like in the other embodiments as described above.

Blood flows into the compartment 10 and, after penetrating the first temperature-control section, it laps the impermeable hollow fiber windings 306, in which water, e.g. heated water, flows, thereby receiving heat and reaching a desired temperature.

The alternation of concavities 5C and 301C impart a wavy motion to blood flows, thereby breaking the laminar flow of blood, and affording improved contact between the latter and the hollow fibers that form the windings 306.

Once blood flows have been heated or cooled in the first temperature-control section, they move into the second oxygenation section 305 through the passages 303.

The wavy motion is also maintained through the passages 303, both due to the profiles of the connection parts 307 that connect the concurrent ends of the partition elements 309 in pairs and due to the profiles of the raised ribs 308 extending from the inner surfaces 3A into the areas in which the passages 303 are formed.

As mentioned above, blood enters the second oxygenation section in which it laps the windings 6 of gas-permeable hollow fibers, thereby receiving oxygen and releasing carbon dioxide, exactly as described above concerning the first embodiment of the device 1 of the invention, which means, in short, that oxygen enters the oxygenation chamber through the inlet 322, flows into the hollow fibers of the windings 6 and is transferred into the blood that laps them, due to differential concentration.

On the other hand, carbon dioxide is transferred from blood to the hollow fibers of the windings 6 and, once it has been collected in the collection chamber 18 with depleted oxygen, it is evacuated through the outlet 323.

The heated water (or other temperature control fluid) enters the temperature control section 304 through the inlet port 321 and comes out of it through the outlet port 320 after flowing past the impermeable capillaries that form the windings 306.

Water and oxygen are prevented from mixing together by the provision of the barriers 338 and 339 that separate the chambers 17, 317 and the chambers 18, 318 and any air in blood is evacuated through the apertures for connection with the outside 324 and 325.

The above described invention has been found to fulfill the intended objects.

The invention so conceived is susceptible to changes and variants within the inventive concept.

Furthermore, all the details may be replaced by other technically equivalent elements; for instance, the direction of flow of the fluids being used may be reversed without affecting the functionality of the inventive principle.

In practice, any material, shape and size may be used as needed, without departure from the scope as defined by the following claims.

The invention claimed is:

1. A device for treating blood in an extracorporeal circulation comprising:
    A box-like shaped body having a first end and a second opposing end and that defines therebetween an inside treating chamber having an internal surface;
    At least one exchanging unit comprising a flat diaphragm, that is impermeable to blood flows and that has two major or larger opposing faces, a greater axis and a smaller axis and is fitted inside said treating chamber, around which a winding of hollow micro-porous fibers is wound;
    At least one inlet port of blood to be treated and an outlet port of treated blood which is axially aligned with said inlet port according to an aligning direction;
    An amassing and delivering space for blood to be treated and a collecting space for treated blood which are defined respectively downstream said inlet port and upstream said outlet port between said exchanging unit and said internal surface, said flat diaphragm being placed with said greater axis parallel to said aligning direction and said smaller axis being placed transverse to said aligning direction, wherein said inlet port and outlet port are co-axially aligned and wherein said diaphragm comprises transverse ribs and straight longitudinal ribs that reciprocally intersect and project in relief from said two major or larger opposing faces and are so distributed as to space said winding from said major or larger opposing faces.

2. A device according to claim 1, wherein said flat diaphragm is one of a plurality of spaced parallel modular diaphragms of said at least one exchanging unit, on which correspondent hollow fiber windings are wound, said spaced parallel modular diaphragms having greater axes parallel to said aligning direction.

3. A device according to claim 2, wherein among said hollow fiber windings dividing members, having greater axes placed parallel to said aligning direction and smaller axes transverse to said aligning direction, are arranged.

4. A device according to claim 3, wherein each of said diaphragms and dividing elements has two major or larger opposing faces which are parallel each other and to said aligning direction, joined by joining ends, each of said major or larger opposing faces being provided with at least one flow-directing recess or cavity and at least one flat or convex surface.

5. A device according to claim 4, wherein said internal surface of said treatment chamber comprises a plurality of blood flow directing recesses or cavities.

6. A device according to claim 4, wherein said at least one flow-directing recess or cavity and at least one flat or convex surface of each of said major or larger opposing faces are staggered in said aligning direction, each of the cavities in any given one of said diaphragms and dividing elements being transversely opposite a respective one of the flat or convex surfaces of an adjacent one of said dividing elements and said diaphragms, each of said flat or convex surfaces of any given one of said diaphragms and dividing elements being transversely opposite a respective one of the recesses or cavities of an adjacent one of said dividing elements and said diaphragms.

7. A device according to claim 2, wherein said diaphragms are reciprocally spaced from each other by a constant or uniform center-to-center distance.

8. A device according to claim 3, wherein said dividing elements are reciprocally spaced from each other by a constant or uniform distance.

9. A device according to claim 1, wherein inside said treatment chamber a thermo-regulator arrangement for thermo regulating the temperature of the blood to be treated is fitted between said inlet port and said exchanging unit, and connected therewith by connecting passages.

10. A device according to claim 9, wherein said thermo-regulator arrangement comprises at least one winding of impermeable capillary elements, wound around a core and designed to be lapped by said blood to be treated.

11. A device according to claim 10, wherein said at least one winding of said thermo-regulator arrangement has a greater axis placed substantially perpendicular to said aligning direction and a smaller axis parallel to said aligning direction, said winding of said thermo-regulator arrangement being arranged inside a thermo-regulation chamber defined inside said treatment chamber, downstream of said inlet port.

12. A device according to claim 11, wherein said at least one winding of said thermo-regulator arrangement is wound around a blood permeable core.

13. A device according to claim 10, wherein said at least one winding of said thermo-regulator arrangement comprises a modular winding having a greater axis oriented substantially parallel to said aligning direction.

14. A device according to claim 13 wherein said thermo-regulator arrangement comprises a plurality of modular windings of impermeable capillary elements, each of said modular windings being wound around a respective core and having a greater axis oriented substantially parallel to said aligning direction, said modular windings all being arranged inside said thermo-regulation chamber.

15. A device according to claim 1, wherein said box-like shaped body further comprises an inlet opening for a thermo-regulator fluid and an outlet opening of said thermo-regulator fluid.

* * * * *